(12) United States Patent
Zaid et al.

(10) Patent No.: US 6,452,036 B1
(45) Date of Patent: Sep. 17, 2002

(54) SYNTHESIS OF DIALKYL CARBONATES

(75) Inventors: Gene H. Zaid, Sterling, KS (US); Beth Ann Wolf, Hutchinson, KS (US)

(73) Assignee: Jacam Chemicals, L.L.C., Sterling, KS (US)

( * ) Notice: Subject to any disclaimer, the term of this patent is extended or adjusted under 35 U.S.C. 154(b) by 0 days.

(21) Appl. No.: 10/139,409

(22) Filed: May 2, 2002

Related U.S. Application Data

(63) Continuation of application No. 10/104,518, filed on Mar. 22, 2002, now abandoned.

(51) Int. Cl.$^7$ ................................................. C07C 69/96
(52) U.S. Cl. ...................................................... 558/277
(58) Field of Search .......................................... 558/277

(56) References Cited

U.S. PATENT DOCUMENTS 6,407,279 B1 * 6/2002 Buchanan et al. .......... 558/277

* cited by examiner

*Primary Examiner*—T. A. Solola
*Assistant Examiner*—Joseph Murray
(74) *Attorney, Agent, or Firm*—Hovey Williams LLP

(57) ABSTRACT

The invention generally concerns methods for the synthesis of dialkyl carbonates, and more specifically dimethyl carbonate (DMC) and diethyl carbonate (DEC). Methods according to the invention generally comprise reacting an alcohol or diol, a base and a halogen in the presence of an amine salt catalyst thereby forming a first intermediate. The first intermediate is reacted with carbon monoxide forming a second intermediate which then reacts with the alcohol or diol in the presence of the amine salt catalyst forming the dialkyl carbonate product.

33 Claims, No Drawings

SYNTHESIS OF DIALKYL CARBONATES

RELATED APPLICATION

This is a continuation of application Ser. No. 10/104,518 filed Mar. 22, 2002 now abandoned.

BACKGROUND OF THE INVENTION

1. Field of the Invention

The invention generally concerns methods for the synthesis of dialkyl carbonates, and more specifically dimethyl carbonate (DMC) and diethyl carbonate (DEC).

2. Description of the Prior Art

Methyl tertiary-butyl ether (MTBE) is a compound used almost exclusively as a fuel additive in gasoline. MTBE is a member of a class of chemicals known as "oxygenates" because they raise the oxygen content of gasoline. MTBE has been used in the United States in low levels as a gasoline additive since the late 1970's to replace lead as an octane enhancer. Since the early 1990's, MTBE has been used at higher concentrations in some gasoline to fulfill the oxygenate requirements of the Clear Air Act Amendments. However, MTBE has been detected in groundwater throughout the United States. MTBE can make drinking water supplies undrinkable due to its offensive taste and odor. While there is limited evidence on the hazards MTBE poses to human health, animal studies have shown MTBE to be a carcinogen.

Because of the environmental problems and potential health risks associated with the use of MTBE, there has been a push to replace MTBE as the oxygenate additive in gasoline. Dialkyl carbonates, especially dimethyl carbonate (DMC) and diethyl carbonate (DEC), have been proposed to replace MTBE as oxygenate gasoline additives because dialkyl carbonates have been shown to be more environmentally friendly and pose fewer health risks than MTBE.

The most traditional method of making dialkyl carbonates has been to react an alcohol with phosgene. This method poses numerous safety hazards derived mainly from the use of phosgene which is highly toxic. Therefore, it was desirable to develop a method of synthesizing dialkyl carbonates without using phosgene.

Alternate methods of synthesizing dialkyl carbonates were developed relying heavily on the use of catalysts in reacting alcohols and carbon monoxide. U.S. Pat. No. 3,114,762 discloses one such method for producing organic carbonates by reacting ethanol and carbon monoxide in the presence of a palladium or platinum catalyst to produce DEC. These catalysts are often expensive and require regeneration from time to time.

U.S. Pat. No. 4,113,762 discloses a method of synthesizing dialkyl carbonates by reacting an alcohol with carbon monoxide and oxygen in the presence of a copper-containing catalyst. However copper-containing catalysts also have certain drawbacks, such as sensitivity to water, which tend to reduce the reaction rate and selectivity of carbon monoxide towards the formation of the dialkyl carbonate.

U.S. Pat. No. 5,118,818 discloses a process for preparing an organic carbonate by directly reacting an alcohol or diol, carbon monoxide, a halogen, and a halide ion. This process is deficient in that it involves endothermic reactions thereby requiring the input of energy in order to drive the reactions toward the desired products. From an economic viewpoint, endothermic reactions are typically not as desirable as exothermic reactions because endothermic reactions proceed at a much slower rate and require that energy be input into the system.

SUMMARY OF THE INVENTION

The current invention provides methods of forming dialkyl carbonates which do not use phosgene as an initial reactant, do not require the use of expensive metal catalysts, and are exothermic in nature thereby eliminating the necessity for providing substantial energy input in driving the reactions toward the desired end products.

Generally, methods according to the invention for forming a dialkyl carbonate having the formula

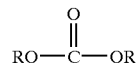

wherein R is a C1–C15 alkyl, alkylene (an organic radical formed from unsaturated aliphatic hydrocarbons), aryl, or aralkyl radical comprise reacting an alcohol or diol having the formula R—OH or HO—R—OH, a base, and a halogen (X) in the presence of an amine salt forming a first intermediate having the formula R—O—X. The first intermediate is reacted with carbon monoxide thereby forming a second intermediate having the formula

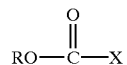

and the second intermediate is reacted with the alcohol or diol in the presence of the amine salt thereby forming the dialkyl carbonate.

In preferred embodiments of the invention, the R radical of the alcohol or diol is selected from the group consisting C1–C8 alkyl, alkylene, aryl or aralkyl radicals. However, preferably the alcohol is a C1–C4 alcohol and even more preferably, the alcohol is selected from the group consisting of methanol, ethanol, and tertbutanol.

Preferably, the halogen for use with the invention is selected from the group consisting of chlorine, bromine, or iodine. Most preferably the halogen is chlorine. The halogen for use with the invention can be in either solid, liquid or gaseous state, however a gas is preferred.

The base used in the reaction can be any base selected from the group consisting of alkali metal salts, alkaline-earth metal salts, tertiary amines, and pyridine. Preferably the base is an alkali or alkaline-earth metal salt selected from the group consisting of alkali and alkaline-earth metal carbonates, bicarbonates, hydroxides, and sulfates. Most preferably, the base will be selected from the group consisting of sodium carbonate, calcium carbonate, magnesium carbonate, sodium hydroxide, calcium hydroxide, and magnesium hydroxide.

The amine salt used with the invention acts as a catalyst in facilitating the ultimate conversion of the reactants into the dialkyl carbonate product. Preferably the amine salt for use with the invention has the formula

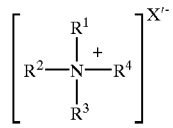

where $R^1$, $R^2$, $R^3$, and $R^4$ are individually selected from the group consisting of H, C1–C22 straight or branched, substituted or unsubstituted alkyl, alkylene (any unsaturated hydrocarbon radical), aryl, or aralkyl radicals, and X is a halide ion. More preferably, the amine salt will comprise a quaternary ammonium salt, and even more preferably comprises a C12–C15 alkyl trimethylammonium chloride salt, wherein $R^1$, $R^2$, and $R^3$ are each a methyl radical and $R^4$ will comprise a C12–C15 straight or branched, substituted or unsubstituted alkyl radical.

In preferred embodiments, the base is present in an amount between about 0.01–25% by weight based on the weight of the alcohol being 100%. Preferably the amine salt is present in an amount between about 0.01–25% by weight based on the weight of the alcohol being 100%.

The dialkyl carbonate product may be separated from the reaction mixture by any means known to those skilled in the art. However, distillation is the preferred method of isolating the dialkyl carbonate product.

DETAILED DESCRIPTION OF THE PREFERRED EMBODIMENT

The following series of chemical equations depict the probable reaction scheme and mechanism employed with the invention and should not be taken as the exclusive reaction scheme and mechanism and nothing therein should be taken as a limitation upon the overall scope of the invention.

For illustrative purposes only, in the following series of equations, the reactants are an alcohol having the formula R—OH, sodium carbonate ($Na_2CO_3$), elemental chlorine ($Cl_2$), and carbon monoxide (CO). A diol may be substituted for the alcohol in the equations, however for the sake of simplicity, only the use of an alcohol will be shown. Likewise, any halogen may be substituted for chlorine. The amine salt catalyst used is an alkyl trimethylammonium chloride salt (R'—$NMe_3$).

The overall reaction scheme comprises three general steps. In the first step, the

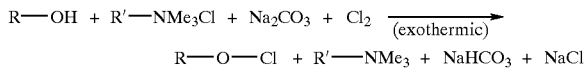

alcohol and chlorine are reacted in the presence of the base and amine salt to form a first intermediate having the formula R—O—Cl.

The second step comprises the reaction of the first intermediate, R—O—Cl, with carbon monoxide to form a second intermediate comprising an alkyl chloroformate. Lastly, the second intermediate quickly reacts with the alcohol in the presence of the base and amine salt to form the final dialkyl carbonate.

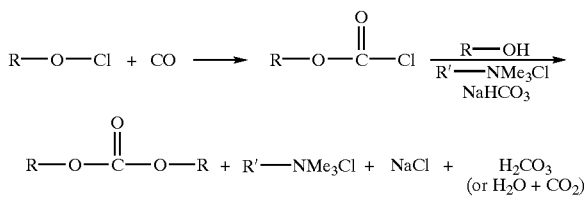

The probable reaction mechanism for the above steps is set forth below. The reaction mechanism generally comprises four steps. In the first step, the hydrogen of

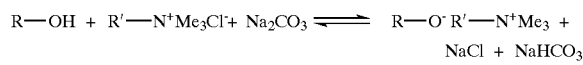

the hydroxyl group of the alcohol is removed.

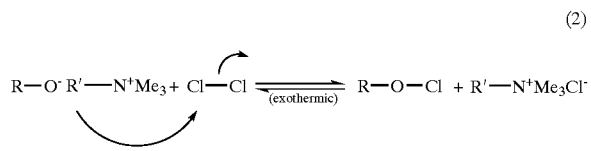

The second step involves the formation of the first intermediate (alkyl hypochloride) described above.

The third step involves the formation of the second intermediate (alkyl chloroformate) described above.

The fourth step involves the reaction of the second intermediate to form the final dialkyl carbonate product.

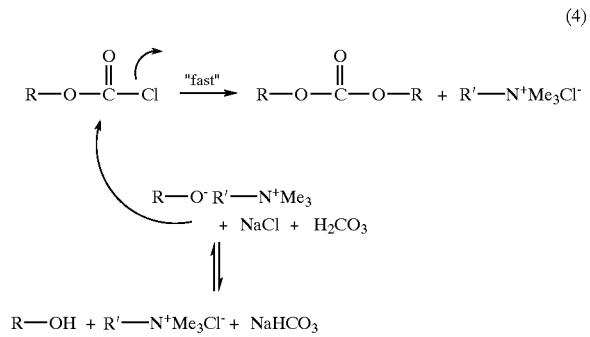

EXAMPLES

The following examples set forth preferred methods according to the invention. It is to be understood, however, that these examples are provided by way of illustration and nothing therein should be taken as a limitation upon the overall scope of the invention.

Example 1

The purpose of this example was to synthesize dimethyl carbonate (DMC). Into a 1-liter stainless steel reaction vessel, 200 ml of methanol, 10 ml of alkyl

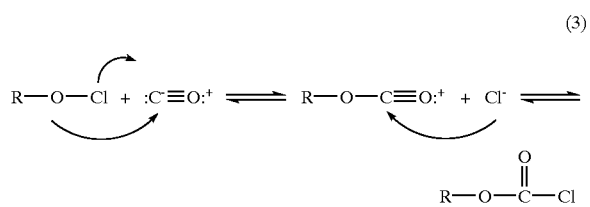

trimethylammonium chloride (WWT 1902W, available from JACAM Chemicals, LLC, Sterling, Kans.) and 10 g of sodium carbonate were added. Next, the reaction vessel was charged with 90 psi of chlorine gas, immediately thereafter the reaction vessel was charged with 180 psi of carbon monoxide. The addition of gases was repeated two times. The a total amount of gases added was approximately 0.81 moles of chlorine and approximately 1.6 moles of carbon monoxide.

Upon the addition of the chlorine to the vessel, an exothermic reaction occurred thereby causing the temperature inside the vessel to rise to approximately 130° F. Upon the addition of carbon monoxide, the temperature further increased to approximately 170° F.

The reaction mixture was allowed to cool to room temperature, a process which took about 15 minutes. The excess gas was removed and the dimethyl carbonate was distilled from the reaction mixture. Approximately 128 ml of DMC were recovered.

Example 2

The purpose of this example was to synthesize diethyl carbonate (DEC). Into a 1-liter stainless steel reaction vessel, 200 ml of ethanol, 10 ml of alkyl trimethylammonium chloride (WWT 1902W, available from JACAM) and 10 g of sodium carbonate were added. Next, the reaction vessel was charged with 90 psi of chlorine gas, immediately thereafter the reaction vessel was charged with 180 psi of carbon monoxide. The addition of gases was repeated two times. The a total amount of gases added was approximately 0.81 moles of chlorine and approximately 1.6 moles of carbon monoxide.

Upon the addition of the chlorine to the vessel, an exothermic reaction occurred thereby causing the temperature inside the vessel to rise to approximately 130° F. Upon the addition of carbon monoxide, the temperature further increased to approximately 170° F.

The reaction mixture was allowed to cool to room temperature, a process which took about 15 minutes. The excess gas was removed and the diethyl carbonate was distilled from the reaction mixture. Approximately 120 ml of DMC were recovered.

Example 3

The purpose of this example was to synthesize diethyl carbonate (DEC). Into a 1-liter stainless steel reaction vessel, 150 ml of ethanol and 15 ml of pyridine were added. Next the reaction vessel was charged with 90 psi of chlorine gas, immediately thereafter the reaction vessel was charged with 180 psi of carbon monoxide. The addition of gases was repeated three times. The a total amount of gases added was approximately 0.81 moles of chlorine and approximately 1.6 moles of carbon monoxide.

Upon the addition of the chlorine to the vessel, an exothermic reaction occurred thereby causing the temperature inside the vessel to rise to approximately 130° F. Upon the addition of carbon monoxide, the temperature further increased to approximately 170° F.

The reaction mixture was allowed to cool to room temperature, a process which took about 15 minutes. The excess gas was removed and the diethyl carbonate was distilled from the reaction mixture. Approximately 22 ml of DEC were recovered.

Example 4

The purpose of this example was to synthesize dimethyl carbonate (DMC). Into a 1-liter stainless steel reaction vessel, 200 ml of methanol, 8 g of potassium hydroxide and 22 ml of pyridine were added. Next the reaction vessel was charged with 90 psi of chlorine gas, immediately thereafter the reaction vessel was charged with 180 psi of carbon monoxide. The addition of gases was repeated two times. The total amount of gases added was approximately 0.81 moles of chlorine and approximately 1.6 moles of carbon monoxide.

Upon the addition of the chlorine to the vessel, an exothermic reaction occurred thereby causing the temperature inside the vessel to rise to approximately 130° F. Upon the addition of carbon monoxide, the temperature further increased to approximately 170° F.

The reaction mixture was allowed to cool to room temperature, a process which took about 15 minutes. The excess gas was removed and the dimethyl carbonate was distilled from the reaction mixture. Approximately 57 ml of DMC were recovered.

Example 5

The purpose of this experiment was to synthesize diethyl carbonate (DEC). Into a 1-liter stainless steel reaction vessel, 200 ml of ethanol, 10 g of potassium hydroxide and 22 ml of pyridine were added. Next the reaction vessel was charged with 90 psi of chlorine gas, immediately thereafter the reaction vessel was charged with 180 psi of carbon monoxide. The addition of gases was repeated three times. The a total amount of gases added was approximately 0.81 moles of chlorine and approximately 1.6 moles of carbon monoxide.

Upon the addition of the chlorine to the vessel, an exothermic reaction occurred thereby causing the temperature inside the vessel to rise to approximately 130° F. Upon the addition of carbon monoxide, the temperature further increased to approximately 170° F.

The reaction mixture was allowed to cool to room temperature, a process which took about 15 minutes. The excess gas was removed and the diethyl carbonate was distilled from the reaction mixture. Approximately 52 ml of DEC were recovered.

Example 6

The purpose of this experiment was to synthesize dimethyl carbonate (DMC). Into a 1-liter stainless steel reaction vessel, 100 ml of methanol, 10 g of potassium hydroxide and 20 ml of trimethyl amine were added. Next the reaction vessel was charged with 90 psi of chlorine gas, immediately thereafter the reaction vessel was charged with 180 psi of carbon monoxide. The addition of gases was repeated three times. The a total amount of gases added was approximately 0.81 moles of chlorine and approximately 1.6 moles of carbon monoxide.

Upon the addition of the chlorine to the vessel, an exothermic reaction occurred thereby causing the temperature inside the vessel to rise to approximately 130° F. Upon the addition of carbon monoxide, the temperature further increased to approximately 170° F.

The reaction mixture was allowed to cool to room temperature, a process which took about 15 minutes. The excess gas was removed and the dimethyl carbonate was distilled from the reaction mixture. Approximately 5 ml of DMC were recovered.

Example 7

The purpose of this experiment was to synthesize ditertiary butyl carbonate (DTBC). Into a 1-liter stainless steel reaction vessel, 100 ml of tert-butyl alcohol, 10 g of sodium hydroxide and 20 ml of trimethyl amine were added. Next the reaction vessel was charged with 90 psi of chlorine gas, immediately thereafter the reaction vessel was charged with 180 psi of carbon monoxide. The addition of gases was repeated three times. The a total amount of gases added was approximately 0.81 moles of chlorine and approximately 1.6 moles of carbon monoxide.

Upon the addition of the chlorine to the vessel, an exothermic reaction occurred thereby causing the temperature inside the vessel to rise to approximately 130° F. Upon the addition of carbon monoxide, the temperature further increased to approximately 170° F.

The reaction mixture was allowed to cool to room temperature, a process which took about 15 minutes. The excess gas was removed and the ditertiary butyl carbonate was distilled from the reaction mixture. Approximately 5 ml of DTBC were recovered.

Example 8

The purpose of this experiment was to synthesize diethyl carbonate (DEC). Into a 1-liter stainless steel reaction vessel, 100 ml of ethanol, 10 ml of alkyl trimethylammonium chloride (WWT 1902W available from JACAM) and 5 g of sodium bicarbonate were added. Next the reaction vessel was charged with 90 psi of chlorine gas, immediately thereafter the reaction vessel was charged with 180 psi of carbon monoxide. The addition of gases was repeated three times. The a total amount of gases added was approximately 0.81 moles of chlorine and approximately 1.6 moles of carbon monoxide.

Upon the addition of the chlorine to the vessel, an exothermic reaction occurred thereby causing the temperature inside the vessel to rise to approximately 130° F. Upon the addition of carbon monoxide, the temperature further increased to approximately 170° F.

The reaction mixture was allowed to cool to room temperature, a process which took about 15 minutes. The excess gas was removed and the diethyl carbonate was distilled from the reaction mixture. Approximately 45 ml of DEC were recovered.

We claim:

1. A method of forming a dialkyl carbonate having the formula

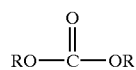

wherein R is a C1–C15 alkyl, alkylene, aryl, or aralkyl radical, comprising:
reacting an alcohol or diol having the formula R—OH or HO—R—OH, a base, and a halogen (X) in the presence of an amine salt forming a first intermediate having the formula R—O—X;
reacting said first intermediate with carbon monoxide forming a second intermediate having the formula

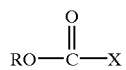

and
reacting said second intermediate and said alcohol or diol in the presence of said amine salt forming said dialkyl carbonate.

2. The method of claim 1, R being a C1–C4 radical.

3. The method of claim 1, said amine salt having the formula

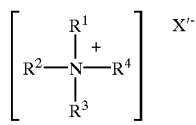

where $R^1$, $R^2$, $R^3$, and $R^4$ are individually selected from the group consisting of H, C1–C22 straight or branched, substituted or unsubstituted alkyl, alkylene, aryl, or aralkyl radicals, and X' is a halide ion.

4. The method of claim 3, said amine salt being a quaternary ammonium salt.

5. The method of claim 4, said quaternary ammonium salt comprising a C12–C15 alkyl trimethylammonium chloride salt.

6. The method of claim 3, X' selected from the group consisting of chloride, bromide and iodide.

7. The method of claim 6, X' being chloride.

8. The method of claim 1, said base selected from the group consisting of alkali and alkaline-earth metal salts, tertiary amines, and pyridine.

9. The method of claim 8, said base selected from the group consisting of alkali and alkaline-earth metal carbonates, bicarbonates, hydroxides, and sulfates.

10. The method of claim 9, said base selected from the group consisting of sodium carbonate, calcium carbonate, magnesium carbonate, sodium hydroxide, calcium hydroxide, and magnesium hydroxide.

11. The method of claim 1, X comprising a halogen gas.

12. The method of claim 1, said base being present between about 0.01–25% by weight based on the weight of alcohol being 100%.

13. The method of claim 1, said amine salt being present between about 0.01–25% by weight based on the weight of alcohol being 100%.

14. The method of claim 1, X being selected from the group consisting of chlorine, bromine, or iodine.

15. The method of claim 14, X being chlorine.

16. A method of forming a dialkyl carbonate having the formula

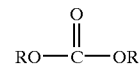

wherein R is a C1–C15 alkyl, alkylene, aryl, or aralkyl radical, comprising:
reacting an alcohol or diol having the formula R—OH or HO—R—OH, a base selected from the group consisting of alkali and alkaline-earth metal salts, tertiary amines, and pyridine, and a halogen (X) in the presence of an amine salt having the formula

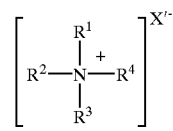

where $R^1$, $R^2$, $R^3$, and $R^4$ are individually selected from the group consisting of H, C1–C22 straight or branched, substituted or unsubstituted alkyl, alkylene, aryl, or aralkyl radicals, and X' is a halide ion, thereby forming a first intermediate having the formula R—O—X;
reacting said first intermediate with carbon monoxide to form a second intermediate having the formula

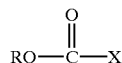

and reacting said second intermediate and said alcohol or diol in the presence of said amine salt forming said dialkyl carbonate.

17. The method of claim 16, X' selected from the group consisting of chloride, bromide, and iodide.

18. The method of claim 17, said halide ion being chloride.

19. The method of claim 16, said base selected from the group consisting of alkali and alkaline-earth metal carbonates, bicarbonates, hydroxides, and sulfates.

20. The method of claim 19, said base selected from the group consisting of sodium carbonate, calcium carbonate, magnesium carbonate, sodium hydroxide, calcium hydroxide, and magnesium hydroxide.

21. The method of claim 16, said base being present between about 0.01–25% by weight based on the weight of alcohol being 100%.

22. The method of claim 16, said amine salt being present between about 0.01–25% by weight based on the weight of the alcohol being 100%.

23. The method of claim 16, R being a C1–C4 alkyl radical.

24. The method of claim 16, said amine salt comprising a quaternary ammonium salt.

25. The method of claim 24, said quaternary ammonium salt comprising a C12–C15 alkyl trimethyl ammonium salt.

26. The method of claim 16, X being selected from the group consisting of chlorine, bromine, or iodine.

27. The method of claim 26, X being chlorine.

28. A method of forming a dialkyl carbonate having the formula

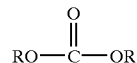

wherein R is a C1–C4 alkyl radical, comprising:

reacting an alcohol or diol having the formula R—OH or HO—R—OH, an alkali or alkaline-earth metal salt, and chlorine in the presence of a quaternary ammonium salt forming a first intermediate having the formula R—O—Cl;

reacting said first intermediate with carbon monoxide forming a second intermediate having the formula:

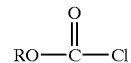

and reacting said second intermediate and said alcohol in the presence of said quaternary ammonium salt forming said dialkyl carbonate.

29. The method of claim 28, said quaternary ammonium salt being a C12–C15 alkyl trimethyl ammonium salt.

30. The method of claim 28, said alkali or alkaline-earth metal salt selected from the group consisting of alkali and alkaline-earth metal carbonates, bicarbonates, hydroxides, and sulfates.

31. The method of claim 30, said metal salt selected from the group consisting of sodium carbonate, calcium carbonate, magnesium carbonate, sodium hydroxide, calcium hydroxide, and magnesium hydroxide.

32. The method of claim 28, said alkali metal salt being present between about 0.01–25% by weight based on the weight of alcohol being 100%.

33. The method of claim 28, said quaternary ammonium salt being present between about 0.01–25% by weight based on the weight of the alcohol being 100%.

* * * * *